(12) United States Patent
Perbost et al.

(10) Patent No.: US 9,962,701 B2
(45) Date of Patent: May 8, 2018

(54) FLOWCELLS WITH MICRORETAINERS AND PARTICLE SEPARATORS FOR DISCRETE SEEDING MICROSPOTS

(71) Applicant: Qiagen Sciences, LLC, Waltham, MA (US)

(72) Inventors: Michel Georges Perbost, Belmont, MA (US); Thomas Daniel Perroud, Lexington, MA (US)

(73) Assignee: QIAGEN SCIENCES, LLC, Waltham, MA (US)

( * ) Notice: Subject to any disclaimer, the term of this patent is extended or adjusted under 35 U.S.C. 154(b) by 0 days. days.

(21) Appl. No.: 15/386,515

(22) Filed: Dec. 21, 2016

(65) Prior Publication Data

US 2017/0182494 A1 Jun. 29, 2017

Related U.S. Application Data

(60) Provisional application No. 62/271,544, filed on Dec. 28, 2015, provisional application No. 62/309,122, filed on Mar. 16, 2016.

(51) Int. Cl.
*B01L 3/00* (2006.01)
*G01N 35/08* (2006.01)
(Continued)

(52) U.S. Cl.
CPC ........ *B01L 3/502761* (2013.01); *B01D 69/02* (2013.01); *B01L 3/5027* (2013.01);
(Continued)

(58) Field of Classification Search
CPC .......... C12Q 1/686; C12Q 2565/501; C12Q 1/6806; B01L 2300/0867;
(Continued)

(56) References Cited

U.S. PATENT DOCUMENTS 7,332,126 B2 2/2008 Tooke et al.
7,642,053 B2 1/2010 Gumbrecht et al.
(Continued)

FOREIGN PATENT DOCUMENTS

KR 20100133939 A 12/2010
WO 2009148507 A1 12/2009
(Continued)

OTHER PUBLICATIONS

International Search Report and Written Opinion for International Application No. PCT/US16/68678, dated Mar. 16, 2017, 12 pages.

*Primary Examiner* — Jennifer Wecker
(74) *Attorney, Agent, or Firm* — RatnerPrestia

(57) ABSTRACT

A flowcell for a sequencing instrument. The flowcell includes a fluid inlet, a fluid outlet, a flow channel formed between an at least partially transparent cover and a base and fluidly connecting the fluid inlet to the fluid outlet, and a capture substrate provided in the flow channel. The capture substrate includes microretainers configured to each receive a single microspot having a microspot diameter, and microretainer is separated from adjacent microretainers by an interstitial gap distance that is equal to or greater than the microspot diameter. A particle separator may be fluidly connected to the flowcell. The particle separator may include a microfluidic channel having an array of micropillars to transfer a plurality of the microspots to a loading buffer that may be delivered to the flowcell.

3 Claims, 8 Drawing Sheets

(51) Int. Cl.

| | | |
|---|---|---|
| *G01N 35/00* | (2006.01) | |
| *B01D 69/02* | (2006.01) | |
| *G01N 35/10* | (2006.01) | |
| *C12N 15/10* | (2006.01) | |
| *B01J 19/00* | (2006.01) | |
| *G01N 15/14* | (2006.01) | |
| *C12M 3/06* | (2006.01) | |
| *B01L 7/00* | (2006.01) | |

(52) U.S. Cl.
CPC .......... *B01L 3/50273* (2013.01); *G01N 35/08* (2013.01); *B01D 2325/06* (2013.01); *B01D 2325/08* (2013.01); *B01J 19/0046* (2013.01); *B01L 3/50857* (2013.01); *B01L 7/52* (2013.01); *B01L 2200/0668* (2013.01); *B01L 2300/0681* (2013.01); *B01L 2300/0816* (2013.01); *B01L 2300/0861* (2013.01); *B01L 2300/0877* (2013.01); *B01L 2300/0893* (2013.01); *B01L 2300/1822* (2013.01); *B01L 2400/0409* (2013.01); *B01L 2400/0487* (2013.01); *B01L 2400/086* (2013.01); *C12M 23/16* (2013.01); *C12N 15/1017* (2013.01); *G01N 15/1484* (2013.01); *G01N 35/1011* (2013.01); *G01N 2015/149* (2013.01)

(58) Field of Classification Search
CPC ....... B01L 2300/0893; B01L 3/502761; B01L 2200/0621; B01L 2200/0631; B01L 2200/0663; B01L 2200/0668; B01L 2200/10; B01L 2200/12; B01L 2300/0681; B01L 2300/0806; B01L 2300/0829; B01L 2300/0838; B01L 2300/0864; B01L 2300/087; B01L 2300/0877; B01L 2300/123; B01L 2400/0409; B01L 2400/0412; B01L 2400/0415; B01L 2400/0421; B01L 2400/0622; B01L 2400/086; B01L 3/0293; B01L 3/5027; B01L 3/502707; B01L 3/502738; B01L 3/508; B01L 3/5085; B01L 3/50857; B01L 7/52; C12M 23/16; C12M 23/12; C12M 47/10; B01D 2325/028; B01D 69/02; B01F 13/0071; B01J 19/0046; B01J 2219/00317; B01J 2219/00459; B01J 2219/005; B01J 2219/00596; B01J 2219/00648; B01J 2219/00655; C12N 15/1017; G01N 15/1484; G01N 2015/149
See application file for complete search history.

(56) References Cited

U.S. PATENT DOCUMENTS

| | | |
|---|---|---|
| 8,481,259 B2 | 7/2013 | Gordon et al. |
| 8,940,481 B2 | 1/2015 | Gordon et al. |
| 9,146,248 B2 | 9/2015 | Hagerott et al. |
| 2003/0040105 A1* | 2/2003 | Sklar .................. B01F 13/0071 435/287.2 |
| 2004/0113316 A1 | 6/2004 | Fujii et al. |
| 2006/0000772 A1* | 1/2006 | Sano .................. B01D 67/0062 210/635 |
| 2006/0252087 A1* | 11/2006 | Tang ........................ G01N 1/40 435/6.12 |
| 2009/0298131 A1 | 12/2009 | Gordon et al. |
| 2011/0283778 A1 | 11/2011 | Angelescu et al. |
| 2011/0301058 A1 | 12/2011 | Cheng et al. |
| 2012/0202709 A1 | 8/2012 | Bergo |
| 2014/0194313 A1* | 7/2014 | Craighead ............. C12M 47/10 506/9 |
| 2014/0267669 A1 | 9/2014 | Stoops et al. |

FOREIGN PATENT DOCUMENTS

| | | |
|---|---|---|
| WO | 2011044116 A2 | 4/2011 |
| WO | 2013162482 A1 | 10/2013 |
| WO | 2015085274 A1 | 6/2015 |

\* cited by examiner

FIG. 3A
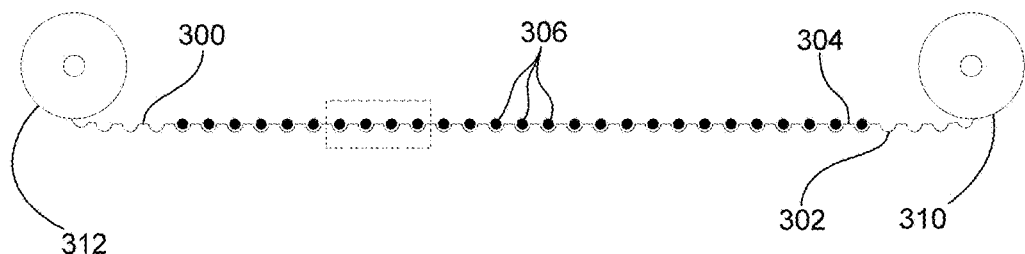
FIG. 3B
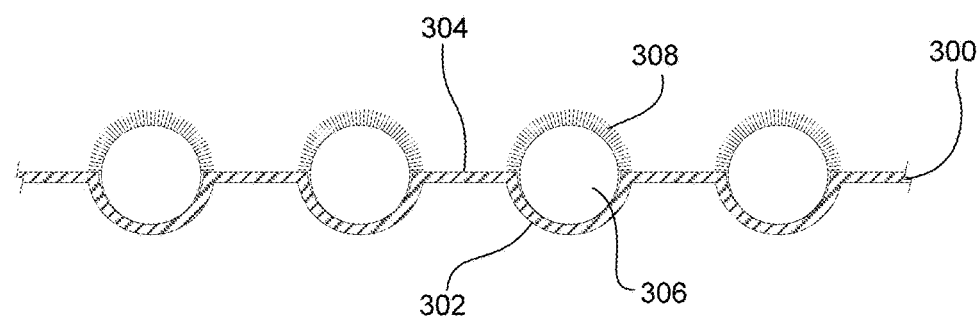
FIG. 3C          FIG. 3D          FIG. 3E
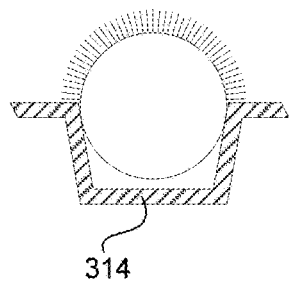 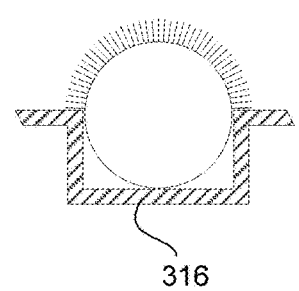 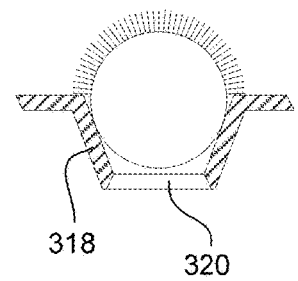

FLOWCELLS WITH MICRORETAINERS AND PARTICLE SEPARATORS FOR DISCRETE SEEDING MICROSPOTS

CROSS REFERENCE TO RELATED APPLICATIONS

This application claims priority to U.S. Provisional Application No. 62/271,544, entitled FLOWCELLS WITH MICRORETAINERS FOR DISCRETE SEEDING MICROSPOTS filed Dec. 28, 2015, and U.S. Provisional Application No. 62/309,122, entitled FLOWCELLS WITH MICRORETAINERS AND PARTICLE SEPARATORS FOR DISCRETE SEEDING MICROSPOTS filed Mar. 16, 2016, the contents of both of which are incorporated herein by reference.

BACKGROUND OF THE INVENTION

Field of the Invention

The present invention relates generally to instruments for performing sequencing-by-syntheses or other sequencing processes, and more particularly to flowcells and particle separators used in such instruments.

Description of the Related Art

DNA (deoxyribonucleic acid) sequencing instruments are used to determine DNA molecular sequences. Such instruments are useful for clinical studies, diagnostics, so-called "personalized medicine" (medical treatment tailored to an individual's genetic content or the like), and so on. Current instruments for performing DNA sequencing use a variety of technologies to analyze the base pairs that form the DNA sequence. For example, some instruments perform sequencing on a library of cloned colonies of single-stranded DNA molecule fragments (DNA template colonies) that are fixed in place inside a flowcell. The flowcell is essentially a small chamber in which the DNA template colonies are subjected to a series of nucleobase extension processes. Each successive extension is detected to determine the base pair sequence of each DNA template colony. The flowcell provides an environment to hold the DNA template colonies during the extension process, and also during the inspection process to read each extended base pair.

Many sequencing-by-synthesis instruments use an optical system such as a microscope to detect the nucleobase extensions, although non-optical systems are also known. A typical optical instrument uses visible chemical labels to determine the identity of each extended base pair. For example, each nucleobase that makes up the DNA molecule (adenine, guanine, cytosine and thymine) may be labeled with a unique fluorescent probe that is visible through the microscope. The label is read each time the DNA template colony is extended, and then the label is removed to make way for the next base pair extension.

In modern "next-generation" instruments, millions of DNA template colonies may be immobilized in a single flowcell, and processed simultaneously. A variety of flowcell designs have been developed to hold the immobilized DNA template colonies, but they usually include certain common features. A typical flowcell includes a rigid flow channel, an optically transparent cover that encloses the channel, and a fluid inlet and a fluid outlet through which the appropriate reagents are passed to control the growth and extension of the DNA template colonies. Examples of such flowcells are found in U.S. Pat. Nos. 8,481,259, 8,940,481 and 9,146,248 and U.S. Patent Application Publication Nos. 2009/0298131 and 2014/0267669, all of which are incorporated herein by reference.

The DNA template colonies may be secured within the flowcell in various ways. For example, clonal DNA template colonies may be secured to individual beads, and then the beads may be secured in a random pattern to a functionalized surface within the flowcell. This technology is useful, but provides little or no control over the spacing of the beads, and thus the DNA template colonies, which can make data acquisition more difficult. This technology also may use separate processing steps outside the flowcell to amplify the DNA templates. This process also may experience relatively inefficient bead capture properties, which may require a greater amount of amplification when preparing the library of DNA templates.

Another technology uses a flowcell having a pattern of organized microwells to immobilize the DNA template colonies. Each well includes a gel functionalized with primers to capture the DNA templates, and the captured templates are amplified to form DNA template colonies in situ within the flowcell. The gel is placed in the wells by coating the entire substrate surface, and then removing the gel from the interstitial space between the individual wells. This process can have several drawbacks. For example, it can lead to additional operating and material costs due to the need to remove a large proportion of the functionalized gel, and any gel that might remain in place can create undesirable interstitial DNA template seeding sites. Also, the gel can be removed accidentally from the well, decreasing the density of the DNA primers.

The inventors have determined that there continues to be a need to advance the state of the art of flowcells for sequencing instruments and similar devices.

SUMMARY

In one exemplary aspect, there is provided a flowcell for a sequencing instrument. The flowcell includes a fluid inlet, a fluid outlet, a flow channel formed between an at least partially transparent cover and a base and fluidly connecting the fluid inlet to the fluid outlet, and a capture substrate provided in the flow channel. The capture substrate has a plurality of microretainers, each configured to receive a single respective one of a plurality of microspots having a microspot diameter, and each of the plurality of microretainers being spaced from each adjacent microretainer by an interstitial gap distance. The interstitial gap distance may be equal to or greater than the microspot diameter.

In some embodiments, the base or the cover may be a flexible film. In some embodiments, the capture substrate may be separate from the cover and the base, and secured to at least one of the cover and the base. Such a capture substrate may be a flexible film having the microretainers formed thereon. Such a film may have the microretainers thermoformed in the film. Such a film may be a polymer, more specifically a cyclic olefin copolymer. Such a film may have a thickness of 1 micrometer to 100 micrometers, 4 micrometers to 50 micrometers, or 10 micrometers to 20 micrometers.

In some embodiments, the microretainers may be wells formed below an interstitial surface between adjacent pairs of microretainers. The microretainers also may be pillars formed above an interstitial surface extending between adjacent pairs of microretainers, and a top of each pillar is configured to receive a respective microspot. The microretainers also may be openings formed between respective groups of micropillars extending upwards from the interstitial surface. Such respective groups of micropillars may be micropillars arranged in a hexagonal pattern. Additional micropillars may be provided on the interstitial surface to prevent the microspots from contacting the interstitial surface.

In some embodiments, the microretainers may be distributed in a triangular pattern with rows arranged along three different axes. In such an embodiment, the three different axes are at 120° relative to one another and the microretainers are in an equilateral triangular pattern.

In some embodiments, the capture substrate may be a plastic material that is embossed or injection molded to form the microretainers.

In some embodiments, the microspots may have a diameter of 300 nanometers to 3 micrometers, 500 nanometers to 1.5 micrometers, or 700 nanometers to 1 micrometer.

In some embodiments, the microretainers may have a depth of approximately 50% of the microspot diameter, or of more than 50% of the microspot diameter.

In some embodiments, the microretainers may have a width that is equal to or greater than the microspot diameter.

In some embodiments, substantially all of the microretainers contain a respective microspot, and each microspot is functionalized with primers for the hybridization of DNA templates but does not include an amplified DNA template colony.

In some embodiments, substantially all of the microretainers contain a respective microspot, and each microspot includes an amplified DNA template colony.

In another exemplary aspect, there is provided a microfluidic particle separator. The microfluidic particle separator may comprise a buffer inlet configured to receive a buffer containing a plurality of microspots, a loading buffer inlet configured to receive a loading buffer, a microfluidic channel configured to receive the buffer containing the plurality of microspots and the loading buffer, and a loading buffer outlet. The microfluidic channel may include an array of micropillars configured to transfer the plurality of microspots from the release buffer to the loading buffer, and the array may be optionally made of a hydrophobic material. The loading buffer outlet may be configured to receive the loading buffer containing the plurality of microspots, and the microfluidic particle separator may be combined with a flowcell, such that the loading buffer outlet is in fluid connection with a fluid inlet of the flowcell.

Other alternatives will be apparent to persons of ordinary skill in the art in view of the present disclosure.

The recitation of this summary of the invention is not intended to limit the claims of this or any related or unrelated application. Other aspects, embodiments, modifications to and features of the claimed invention will be apparent to persons of ordinary skill in view of the disclosures herein.

BRIEF DESCRIPTION OF THE DRAWINGS

A better understanding of the exemplary embodiments may be understood by reference to the attached drawings, in which like reference numbers designate like parts. The drawings are exemplary and not intended to limit the claims in any way.

FIG. 3A is a schematic elevation view of a second exemplary embodiment of a capture substrate and associated microspots.

FIG. 3B is a detail view of a portion of the embodiment of FIG. 3A.

FIG. 3C is a detail view of a portion of the embodiment of FIG. 3A, illustrating an alternative microretainer shape.

FIG. 3D is a detail view of a portion of the embodiment of FIG. 3A, illustrating another alternative microretainer shape.

FIG. 3E is a detail view of a portion of the embodiment of FIG. 3A, illustrating still another alternative microretainer shape.

DETAILED DESCRIPTION

The inventors have identified a variety of alternative flowcell structures and methods that may be used with DNA sequencing instrument or similar devices, such as those provided in the inventors' copending application No. 62/271,544 filed on Dec. 28, 2015, the entire contents of which are incorporated herein by reference. Non-limiting examples of such structures and methods are provided herein.

Figure 1:
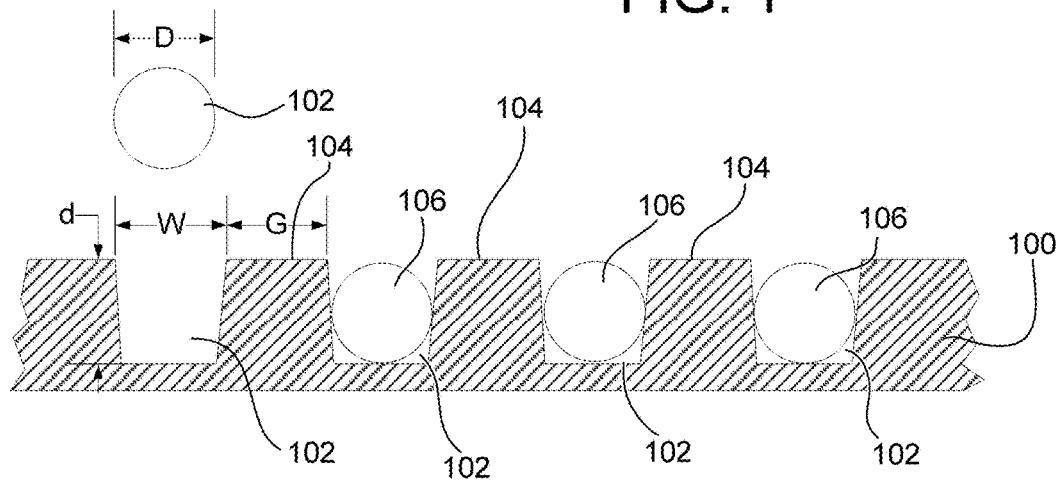
FIG. 1 is schematic elevation view of a first exemplary embodiment of a capture substrate and associated microspots.
Figure 2:
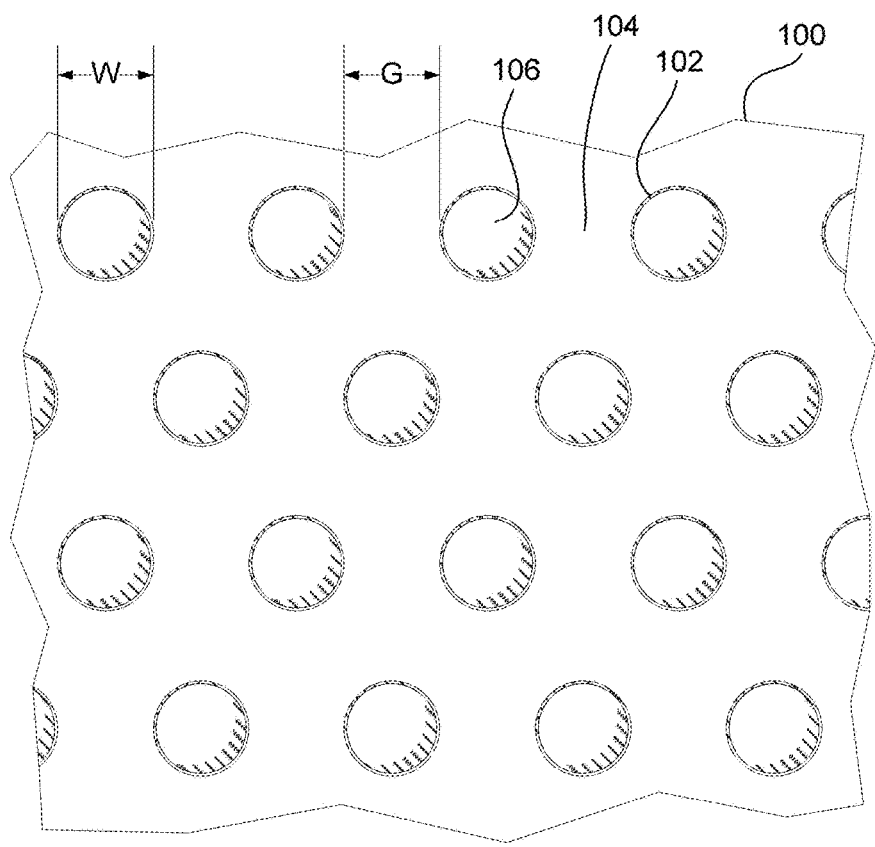
FIG. 2 is a partial plan view of the embodiment of FIG. 1.

FIGS. 1 and 2 are side and top views of a capture substrate 100. The substrate 100 has a plurality of microretainers 102 formed as frustoconical wells in an upper surface of the substrate 100. Raised regions 104 are provided between each adjacent pair of microretainers 102, and the tops of the raised regions 104 define the upper surface of the substrate 100. Each microspot 106 is configured to hold a DNA template colony comprising a plurality of clonal DNA template strands. For purposes of illustration, the microspot 106 at the far left of FIG. 1 is shown removed from its respective microretainer 102, but in use it would be secured within the microretainer 102 as the other microspots 106 are shown. As explained more below, the substrate 100 may comprise an internal surface of a flowcell, or it may be a separate part that is provided in a flowcell.

The substrate 100 may comprise metal, glass, rigid plastic, ceramic, film or any other suitable material. The substrate 100 preferably is relatively flat so as to present the DNA template colonies secured thereto in a flat plane that lies within the depth of field of a microscope or other optical instrument used to read the DNA template colonies during the sequencing process.

The microretainers 102 are separated by interstitial raised regions 104. In the embodiment of FIGS. 1 and 2, the raised regions 104 join together to form a continuous upper surface of the substrate 100, but in other embodiments, the raised regions 104 may comprise a plurality of discrete regions extending upward from a lower surface. For example, the wells that form the microretainers 102 may be joined by channels that divide the raised regions 104. Each raised region 104 provides an interstitial gap G between an adjacent pair of microretainers 102. The width of every interstitial gap G preferably is equal to, and more preferably greater than, the microspot diameter D. However, in some embodiments, the interstitial gap distance G between certain ones or all of the microspots may be less than the microspot diameter D.

The microretainers 102 and raised regions 104 may be formed using any suitable fabrication method. For example, the microretainers 102 can be selectively etched away from the upper surface of the substrate 100, while leaving the raised regions 104 in place as the unetched portion of the substrate 100. Wet (e.g., chemical) or dry (e.g., plasma) photolithography or etching processes may be used by coating the portions of the substrate 100 that are not to be etched with a photoresist or other neutral layer, applying the desired etching medium to form the microretainers 102, and then optionally removing the photoresist coating. The microretainers 102 and raised regions 104 also may be made by additive manufacturing techniques, such as the sol-gel process or microscopic material deposition or printing, in which material is built up on the original upper surface of the substrate 100 to form the raised regions 104 with the microretainers 102 therebetween. Certain substrate 100 materials, such as plastic, also may be manufactured using molding techniques (e.g., injection molded) or embossing. Other alternatives will be apparent to persons of ordinary skill in the art in view of the present disclosure.

The microretainers 102 may be distributed in any desired pattern, such as a rectilinear or square grid pattern or rows or columns, a triangular pattern having rows oriented along three axes, and so on. In a preferred embodiment, the microretainers 102 are provided in an equilateral triangle pattern with the microretainers 102 lying in rows that are oriented at 120° relative to one another, such as shown in FIG. 2. This arrangement may be beneficial to maximize the number of microretainers 102 provided within a given substrate area, while still maintaining a minimum desired interstitial gap G between each adjacent pair of microretainers 102.

The microspots 106 may comprise any suitable structure that can be functionalized with primers for the hybridization of DNA templates. In a preferred embodiment, the microspots 106 are spherical, but they may be other shapes. The microspots 106 may be solid, such as glass beads. Alternatively, the microspots 106 may comprise a porous material, such as a polymer bead, to increase the surface area of the microspots 106 and enhance the density of primers on the microspot's surface. The microspots also may be transparent, which can potentially increase the intensity of fluorescing light that is visible to an associated optical microscope or the like. Transparent microspots also may allow an associated microscope to detect light reflecting off the substrate below the microspot 106.

The microspots 106 may have any suitable diameter D. In a preferred embodiment, the microspot diameter D may be in the range of 300 nanometers ("nm") to 3 micrometers ("µm"). In another preferred embodiment, the microspot diameter D may be in the range of 500 nm to 1.5 µm. In still another preferred embodiment, the microspot diameter D may be in the range of 700 nm to 1 µm. For purposes of this disclosure, the diameter D of a non-spherical microspot 106 will be understood to be the diameter of a spherical object having the same volume (including the internal porosity, if the material is measurably porous) as the non-spherical microspot 106. The foregoing microspot dimensions are expected to have utility in relation to fluorescent methods of base pair extension detection. Other microspot diameters, such as smaller or larger diameters, may be used in other embodiments, and the diameters may be selected specifically for the type of detection intended to be used.

Each microretainer 102 preferably is sized to retain a single microspot 106. The microretainers 102 preferably are also configured to hold each microspot 106 with approximately one-half or less of the microspot's surface lying above the upper surface of the substrate 100. In some embodiments, the microretainer 102 may be deep enough to fully contain the microspot 106, so that the microspot 106 does not protrude above the interstitial surface 106, such as shown in FIG. 1. It will be appreciated that the degree to which the microspots 106 fall below the upper surface of the substrate 100 can be affected by one or more of the microretainer shape, the microretainer depth d, and the microretainer width W. For example, where spherical microspots 106 are used and the microretainer 102 comprises a deep cylindrical shape having a width W that is less than the microspot diameter D, the microspots 106 may rest on the upper edge of the microretainer 102 without dropping to the full depth d of the microretainer 102. To have less than 50% of the microspot's surface above the upper surface of the substrate 100, the microretainer depth d preferably is equal to or greater than approximately 50% of the microspot diameter D, and the microretainer width W preferably is equal to at least 100% of the microspot diameter D. The microretainers 102 also may have a depth d and width W that both are equal to or greater than the microspot diameter D, such that the entire microspot 106 is held below the upper surface of the substrate 100. In a preferred embodiment, the microretainers 102 may have a depth d in the range of 150 nm to 1.5 µm, and a width W in the range of 300 nm to 3 µm. In another preferred embodiment, the microretainers 102 may have a depth d in the range of 250 nm to 0.75 µm and a width W in the range of 500 nm to 1.5 µm. In still another preferred embodiment, the microretainers 102 may have a depth d in the range of 350 nm to 0.5 µm and a width W in the range of 700 nm to 1 µm.

The microretainers 102 also may be shaped to correspond to the shapes of the microspots 106. For example, where the microspots 106 are spherical, the microretainers 102 may be hemispherical, such as in the embodiment of FIG. 3B. The microretainers 102 also may have a parabolic or lens-like shape to help direct fluorescing light perpendicular to the substrate 100. The microretainers 102 also may have different plan profile shapes (i.e., the shape as viewed perpendicular to the plane of the substrate 100). For example, the microretainers 102 may comprise rectangular or square plan profile shapes, or hexagonal plan profile shapes. The sides of the microretainers 102 that extend down from the raised regions 104 also may have different depth profile shapes (i.e., the shape as viewed parallel to the plane of the substrate 100), such as straight shapes, tapered shapes, curved shapes, and so on.

FIGS. 3A and 3B illustrate another embodiment of a substrate 300 formed from a thin film, with FIG. 3B being a detail view of the portion of FIG. 3A that is shown in a dashed box. An example of a thin film is a polymer, such as a cyclic olefin copolymer film having a thickness of 1 to 100 µm, 4 to 50 µm, or 10 to 20 µm, but other alternatives may be used in other embodiments. In this example, the microretainers 302 may be embossed or thermoformed in the film. United States Patent Publication No. 2004/0113316, which is incorporated herein by reference, provides examples of methods for forming micron-dimensioned features in films, and other techniques will be readily apparent to the person of ordinary skill in the art in view of the present disclosure. Raised regions 304 are formed by interstitial portions of the film substrate 300 lying between adjacent pairs of microretainers 302. The raised regions 304 and microretainers 302 may be formed simultaneously during an embossing process, a thermoforming process, or by other processes.

Each microretainer 302 is configured to hold a single microspot 306. The shapes and dimensions of the microspots 306 and microretainers 302 may be selected as described above, or using other criteria. In the shown example, the microspots 306 are spherical, and the microretainers 302 are hemispherical (i.e. a circular plan profile shape and a semicircular depth profile shape) and sized to hold the microspots 306 with about 50% or more of each microspot's surface below the upper surface of the substrate 300. In this configuration, it is expected that clonal DNA template colonies 308 will primarily be present on the exposed upper surface of the microspot 306.

FIG. 3C shows an alternative embodiment in which the microretainers 314 are shaped as frustoconical cups (i.e., a tapered or trapezoidal depth profile shape), instead of hemispheres. FIG. 3D shows another alternative embodiment in which the microretainers 316 are cylindrical cups (i.e., a straight-walled and rectangular depth profile shape). The microretainers 314 alternatively may be cubic, hexagonal, or shaped otherwise. These and other alternative shapes may be used in any of the foregoing embodiments or in other embodiments. It is also envisioned that the microretainers 302 may comprise perforations through the film substrate 300, in which case each microspot 306 will be retained with a portion of the microspot exposed below the substrate 300. An example of this structure is shown in FIG. 3E, in which the microretainers 318 are frustoconical cups with an open bottom 320. The use of perforated microretainers 302 may provide greater access to reagents, expand the scope of technologies available to form the microretainers 302 in the film substrate 300, or provide other benefits. Other alternatives will be apparent to persons of ordinary skill in the art in view of the present disclosure.

The film substrate 300 may comprise a flexible material that may be integrated into a flowcell in a number of different ways. For example, the substrate 300 may be provided on a supply roll 310 and removed on a waste roll 312. Details and other embodiments of the use of thin films in flowcells are provided in the inventors' copending application No. 62/271,423 filed on Dec. 28, 2015, the entire contents of which are incorporated herein by reference. Other alternatives will be apparent to persons of ordinary skill in the art in view of the present disclosure.

Embodiments of a substrate may be configured to immobilize the microspots in the microretainers in any suitable manner. For example, the substrate and microspots may be joined by biotin-streptavidin bonds, covalent bonds, electrostatic interactions, Van der Waals forces, and so on. To this end, the microretainers and/or microspots may be chemically functionalized to bond together. For example, the entire substrate may be functionalized with a bonding chemistry, and then the raised regions are cleansed of the bonding chemistry to prevent bonding anywhere but in the microretainers. As another example, the substrate may be treated with a mask (e.g., a photoresist or the like) that covers the raised regions before the bonding chemistry is applied. In this embodiment, the mask may be the same mask that is used in the initial step of forming the microretainers, in which case the mask may be applied, the microretainers formed, the microretainers functionalized to be able to immobilize the microspots, and then the mask is removed. The microspots also may be retained by gravity, magnetic attraction, or combinations of mechanisms. Other alternatives will be apparent to persons of ordinary skill in the art in view of the present disclosure.

Figure 4:
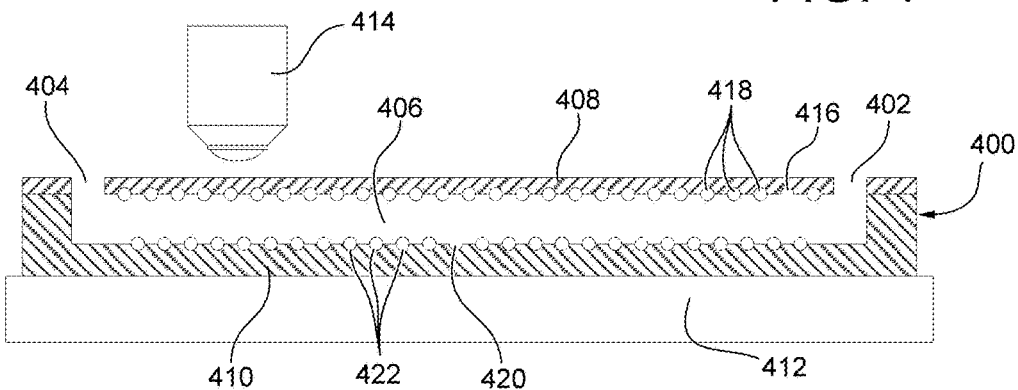
FIG. 4 is a schematic elevation view of a first exemplary flowcell and associated instruments.

Embodiments of a substrate may be incorporated into flowcells for use in sequencing instruments and the like. FIG. 4 illustrates a flowcell 400 having a fluid inlet 402, a fluid outlet 404 and an enclosed channel 406 extending from the inlet 402 to the outlet 404. The channel 406 is formed between a cover 408 and a base 410. At least a portion of the cover 410 comprises a transparent window through which the channel 406 is visible. The flowcell 400 may be mounted on a thermoelectric heating/cooling device 412 (e.g., a so-called "Peltier" device), which is used to thermally cycle the contents of the flowcell 400, as known in the art. The flowcell 400 may be positioned below a microscope 414 or other optical instrument used to detect fluorescent labels to identify each nucleobase extension during the sequencing process. The flowcell 400 may be entirely or partially removable from the rest of the instrument, or permanently integrated as part of the instrument. Other alternatives will be apparent to persons of ordinary skill in the art in view of the present disclosure.

In the embodiment of FIG. 4, the cover 408 and the base 410 are both configured as substrates, such as those described above. For example, the inner surface of the cover 408 (i.e., the surface facing the channel 406) may comprise a glass material that is etched to form a plurality of upper microretainers 416 that are configured to hold a first population of microspots 418. Similarly, the inner surface of the base 410 (i.e., the surface facing the channel 406) may comprise a metal material that is etched to form a plurality of lower microretainers 420 that are configured to hold a second population of microspots 422. (The sizes of the microretainers 416 and microspots 422 in this and other illustrations herein are greatly exaggerated for illustration purposes.) The first and second populations of microspots 418, 422 may be generally identical except for their immobilization location within the flowcell 400, but it is envisioned that the upper and lower microretainers 416, 420 may be configured to hold different kinds, arrangements, patterns, or population densities of microspots 422. In other embodiments, the microretainers may be provided only on the cover 408 or only on the base 410.

Figure 5:
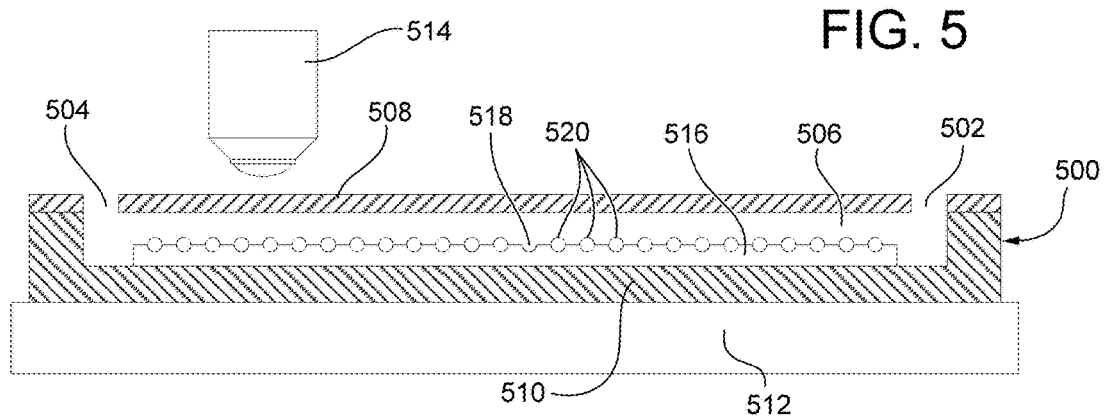
FIG. 5 is a schematic elevation view of a second exemplary flowcell and associated instruments.

FIG. 5 illustrates another example of a flowcell 500 incorporating an embodiment of a substrate. Once again, the flowcell 500 includes a fluid inlet 502, a fluid outlet 504, and a channel 506 forming a fluid passage from the inlet 502 to the outlet 504. The channel 506 is provided between an at least partially-transparent cover 508, and a base 510. The flowcell 500 may be mounted on a heating device 512, and below a microscope 514 or the like.

In the embodiment of FIG. 5, a substrate 516 is provided as a separate part that is joined to the base 510 and/or cover 508. The substrate 516 may comprise a generally rigid material, such as a plastic, glass or metal sheet, that maintains a flat shape. The substrate 516 includes a plurality of microretainers 518 that hold microspots 520. This arrangement allows the shape and size of the substrate 516 to be custom-designed to fit into pre-existing flowcells, and to provide greater flexibility in the sequencing process. For example, a flowcell may be provided with a variety of different interchangeable substrates 516 to allow the instrument operator to select the number, geometric orientation, and/or spacing between the microretainers. Also, multiple different substrates 516 (or a single substrate 516 having multiple different configurations) can be placed in a single flowcell for simultaneous processing. This may be particularly useful to allow certain portions of the substrate 516 to act as a control region or as a comparison region for the remaining portions of the substrate 516. For example, a portion of the substrate 516 may have larger interstitial gaps G to provide a region with higher microspot differentiation qualities to help establish baseline label fluorescent intensity values. Such variations in the spacing or other properties of the microretainers may be used in other embodiments, as well.

Figure 6:
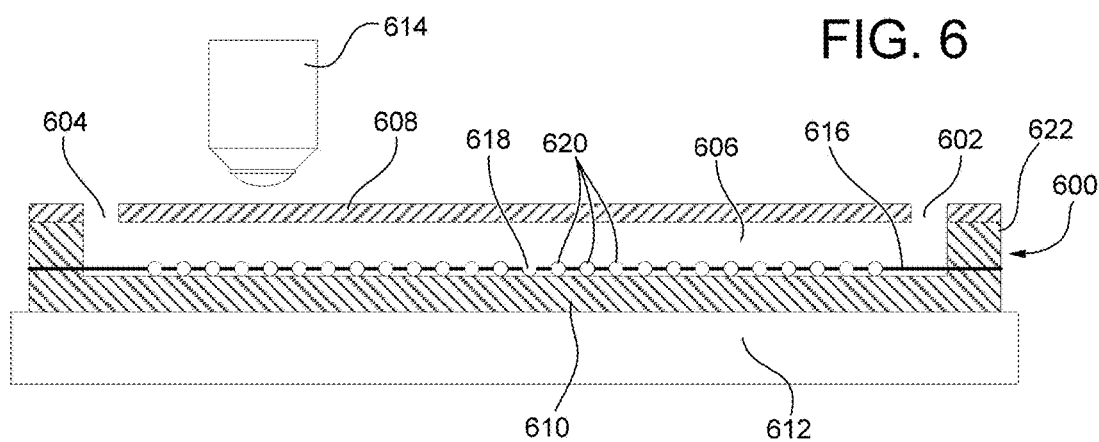
FIG. 6 is a schematic elevation view of a third exemplary flowcell and associated instruments.

FIG. 6 illustrates another example of a flowcell 600 incorporating an embodiment of a substrate. The flowcell 600 includes a fluid inlet 602, a fluid outlet 604, and a channel 606 forming a fluid passage from the inlet 602 to the outlet 604. The channel 606 is provided between an at least partially-transparent cover 608, and a base 610. The flowcell 600 may be mounted on a heating device 612, and below a microscope 614 or the like.

In this embodiment, a substrate 616 is provided as a thin film that is formed to include microretainers 618 that hold microspots 620. The film is flexible and does not necessarily maintain a flat shape without being held in place by other parts. The substrate 616 may be incorporated into the flowcell 600 using any suitable construction or parts. For example, the substrate 616 may be stretched flat against the base and pinched in place between a vertical wall 622 that forms the perimeter of the flowcell 600, and an upper surface of the base 610. Alternatively, the substrate 616 may be held in place by a differential pressure applied across the two sides of the film, as discussed in the above-mentioned copending application by the present inventors. Other alternatives will be apparent to persons of ordinary skill in the art in view of the present disclosure, and other embodiments are discussed and incorporated by reference in the preceding disclosure.

Figure 7A:
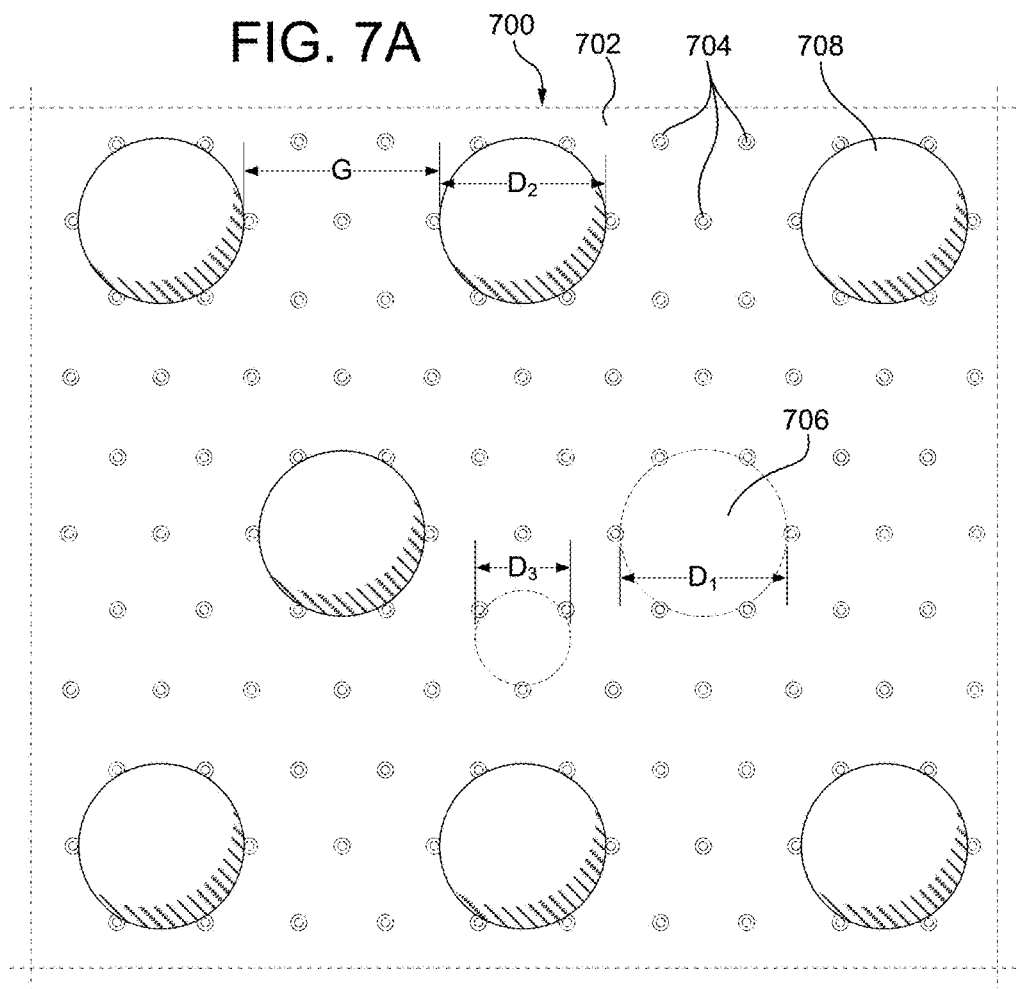
FIGS. 7A and 7B are top plan and inclined views of another exemplary embodiment of a capture substrate and associated microspots.
Figure 7B:
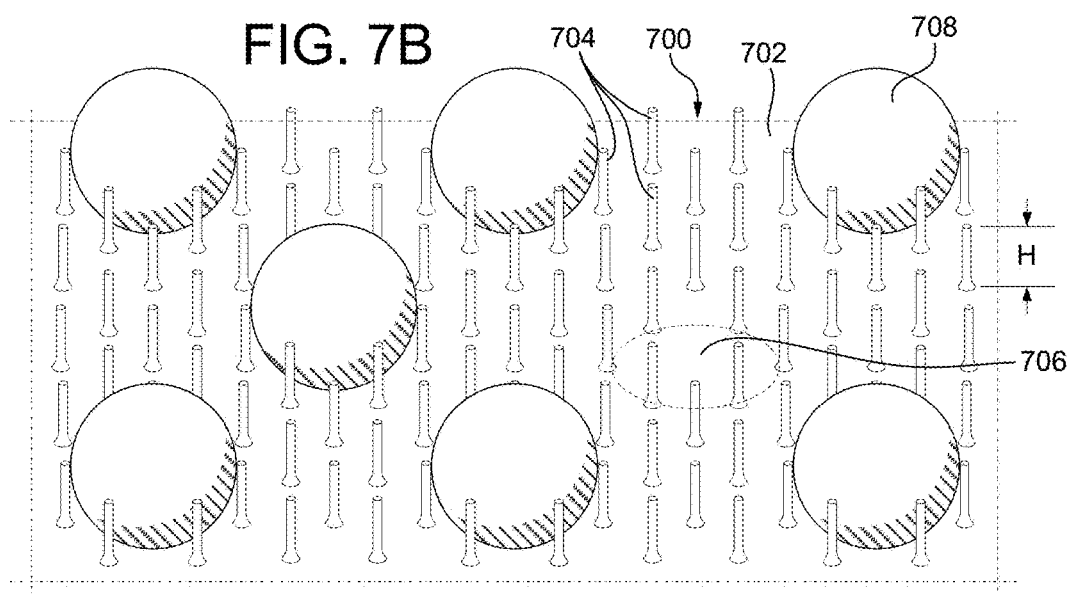

FIGS. 7A and 7B illustrate another example of a capture substrate 700. (For clarity, only a portion of the substrate is shown.) The substrate 700 comprises a flat lower surface 702 from which a plurality of micropillars 704 extend upwards. The micropillars 704 are arranged in a pattern that forms discrete microretainers 706 into which microspots 708 fit, in order to capture the microspots 708 on the substrate 700. More specifically, each microretainer 706 is formed as an open space surrounded by a plurality of micropillars 704, with the open space being sized to receive a single microspot 708. For example, groups of six micropillars 704 may be arranged in hexangular patterns to form openings having a diameter $D_1$ that is approximately equal to or somewhat greater than the diameter $D_2$ of the microspots 708. If the microspots 708 are expected to have some variability in their diameters $D_2$ (e.g., a coefficient of variation of 3%, or the like) the microretainer effective diameter $D_1$ may be selected to encompass a desired proportion of the expected microspot diameters $D_2$. The microretainers 706 are arranged in a triangular pattern or repeating rows that are oriented at 120° relative to one another. This pattern is expected to provide maximum microspot density for a given interstitial gap distance G. Other embodiments may use other arrangements, such as by orienting the microretainers 706 in a square or rectangular pattern of rows oriented at 90° relative to one another. Other alternatives will be apparent to persons of ordinary skill in the art in view of the present disclosure.

In the embodiment of FIGS. 7A and 7B, the microspots 708 are free to drop all the way down to contact the lower surface 702, but this is not required in all embodiments. Also, other embodiments may use different patterns of micropillars 704 to form the microretainers 706, such as an arrangement of four micropillars 704 at the corners of a square, and so on. The particular dimensions of the microspot diameter D1 may be selected according to the microspot sizes discussed above, or to other dimensional specifications.

The micropillars 704 are arranged in the remaining portions of the substrate 700 (i.e., the portions between the microretainers 706) in such a way that they prevent the microspots 708 from dropping down far enough to be effectively captured in place. For example, in regions outside the microretainers 706, the micropillars 704 may be arranged in a repeating triangular pattern having an effective diameter $D_3$ that is too small to allow more than about 10% or less of the diameter $D_2$ of the microspots 708 to drop below the upper plane of the micropillars 704. Thus, any microspots 708 that might come to rest upon the micropillars 704 at locations besides the microretainers 706 may be easily swept away by a flow of reagent or other solution or by tilting the substrate 700. The regions of the substrate 700 between the microretainers 706 form an interstitial gap G between adjacent microretainers 706. The gap G preferably is equal to, and more preferably greater than, the microbead diameter $D_2$, to help prevent polyclonality caused by interstitial contamination.

The height H of the micropillars 704 preferably is selected to capture the microbeads 708 in place by providing mechanical resistance to the microbeads' 708 movement. For example, the micropillar height H may be equal to or more preferably greater than half of the microspot diameter $D_2$. As another example, the micropillar height H may be between 50% and 100% of the microspot diameter $D_2$. Other heights may be used in other embodiments.

The foregoing embodiment may be modified in various ways. For example, the lower surface 702 may include a chemical treatment to bond the microspots 708 in place. In this case, the micropillars 704 may be used to establish where the microspots 708 can contact the lower surface 702, but may not be relied upon to capture the microspots 708 in place. Thus, the micropillar height H may be reduced. The pattern of the microretainers 706 also may be modified to obtain different distribution patterns and densities of microspots 708. As with other embodiments described herein, the distribution pattern and density may be selected to maximize the number of microspots to increase data volume, reduce the number of microspots to increase data accuracy by reducing cross-talk and the like, and so on. In still another example, the microretainers 706 may have short micropillars located within them to prop up the microspot 708 slightly above the lower surface 702, which can enhance reagent exposure and template growth, and help reduce the size and intensity of patterns of fluorescing light that might reflect off the lower surface. In yet another example, the micropillars 704 may be configured to hold the microspots 708 at a variety of different distances from the lower surface 702. Other alternatives will be apparent to persons of ordinary skill in the art in view of the present disclosure.

The use of micropillars 704 to form the microretainers 706 is expected to provide several benefits. For example, the microspots 708 will have better access to reagents, and can potentially grow larger DNA colonies that will provide enhanced visibility during the reading process. Furthermore, excess reagent may be more readily removed by convection flow, instead of relying solely on diffusion.

A substrate 700 having micropillars may be made using any suitable technique. For example, micropillars 704 may be formed using photolithography and electroplating methods, molding or thermal forming of thin films, pulsed or time-multiplexed etching, deep-reactive ion etching (to form molds), and so on. Other alternatives will be apparent to persons of ordinary skill in the art in view of the present disclosure.

Figure 8:
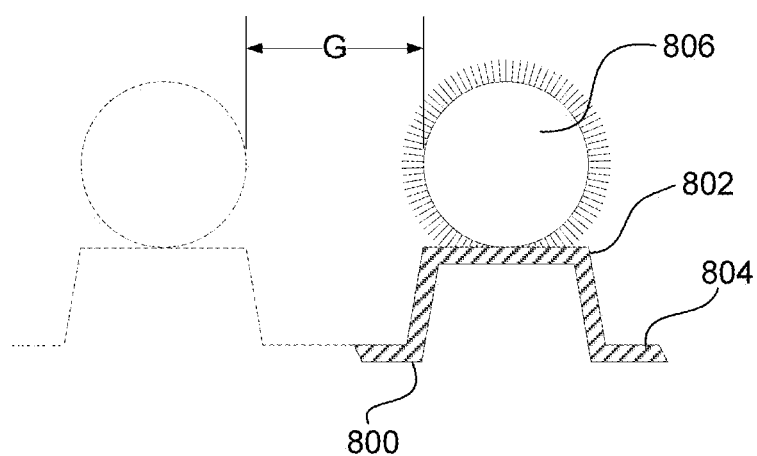
FIG. 8 is a schematic elevation view of another exemplary embodiment of a capture substrate and an associated microspot.

FIG. 8 schematically illustrates another embodiment of a retainer substrate 800 having microretainers 802 in the form of pillars that extend upwards from a lower surface 804. Unlike the previous embodiment, the microspot 806 is captured in place on top of the microretainer 802, such as by providing a suitable chemical composition to provide such capture. The lower surface 804 provides a gap G between adjacent microspots 806, such as described previously herein. This embodiment may offer greater reagent access to the microspots 806, because the microspots 806 are suspended above the surrounding interstitial lower surface 804, while still maintaining suitable gap distance G to mitigate polyclonality caused by interstitial contamination.

The foregoing specification describes three different general configurations of microretainers for capture substrates: microretainers formed as wells that extend below an interstitial surface, microretainers formed by gaps between micropillars that form an interstitial space, and microretainers formed by pillars upon which the microspots are captured. Embodiments may use a single one of these configurations, or combinations of one or more of these configurations.

The substrate, and flow cells having substrates, may be used in any suitable manner. In one example, the microspots may be functionalized with a universal DNA primer specific to the DNA templates of interest before the microspots are introduced to the flowcell. The primer may be attached to the microspot using any suitable bond, such as a covalent bond, a biotin-streptavidin bond, electrostatic interactions, or Van der Waals forces. For example, a covalent bond with the primer may be formed by silanization for glass and plastic microspots surfaces, or by thiol functionalities for gold surfaces and the like. Other methods for attaching primers to microspots will be understood by persons of ordinary skill in the art in view of the present disclosure.

The functionalized microspots are loaded by introducing them into the flowcell, where the microretainers capture and immobilize the microspots, preferably with no more than one microspot per microretainer. It will be appreciated that some microretainers may remain empty, and some microretainers may hold multiple microspots, but it is preferred for the vast majority of microretainers to hold a single microspot. Once the microspots are loaded, the DNA templates of interest are progressively loaded into the flowcell, so that a single DNA template will bind to each microspot. Next, each DNA template is amplified within the flowcell, to the extent of primer availability. In an alternative embodiment, the seeding process (loading the DNA templates) and amplification may be performed simultaneously. In another alternative embodiment, the microspots are functionalized and seeded with a DNA template before being introduced to the flowcell. In still another embodiment, the microspots may be functionalized, seeded and amplified before introducing them to the flowcell. Other alternatives will be apparent to persons of ordinary skill in the art in view of the present disclosure. The sequencing by synthesis process begins after amplification is complete.

The use of the foregoing method with embodiments of microretainers and microspots may provide several benefits. For example, the amount of amplification is limited by the availability of primers on the exposed surface of the microspot, rather than the amplification time. This limitation helps control and normalize the sizes of the different DNA template colonies that form during amplification, so that the different colonies tend to have similar shapes and a narrower and more uniform distribution of colony sizes. This helps provide more uniform fluorescence signal during the sequencing by synthesis process, which can improve base pair detection and data processing.

Furthermore, the microretainer density—and more specifically the size of the interstitial gap G—can be selected to reduce or minimize the incidence of polyclonality (i.e., amplification of different DNA templates on a single microspot) caused by interstitial contamination. This also helps improve data quality by removing overlapping signals and improving the purity of the signal at each microspot. It is expected that an interstitial gap G that is equal to or greater than the microspot diameter D will be effective for this purpose, but other interstitial gap G sizes may be used, such as a gap G size that is less than the microspot diameter D.

The distribution of the microretainers can also be selected to change the quantity and quality of the sequencing data. For example, a denser spacing may be used to increase quantity, and a less dense spacing may be used to increase quality. The microretainer density can also be tailored to provide greater flexibility in the data output generated within the flowcell for different sequencing applications, depending on the particular needs of each application. Embodiments of the substrate are expected to allow the flexibility to change the microretainer pattern and spacing with little or no added cost or inconvenience, to achieve variable loading and output capacity within the same flowcell surface area. Furthermore, the fact that the microretainer locations dictate the spatial distribution of the DNA template colonies can be used to simplify the data analysis process, because it can take less computational effort to establish the physical location of each DNA template colony location, especially in systems in which it is necessary to re-register the colony locations between consecutive sequencing cycles.

Another advantage of the method described above is that the support on which the DNA template colonies is grown is functionalized with primers while it is separate from the retaining substrate. Thus, there is less waste of primers and no need for additional steps to remove primers from undesired locations on the substrate, particularly as compared to systems that apply a functionalized gel to the entire substrate and then remove the gel from areas between the desired DNA template colony locations.

Furthermore, while the embodiments described herein have generally been explained in the context of sequencing by syntheses processes, it will be appreciated that embodiments may be configured for use in other processes that require placement of micro- and nano-scale objects in a flowcell. For example in yet another embodiment of the present invention, a capture substrate having a plurality of micropillars, similar to the embodiment illustrated in FIGS. 7A and 7B, may be used for microfluidic particle separation and/or at least partially removing the oil phase in an emulsified sample containing target particles.

Figure 9A:
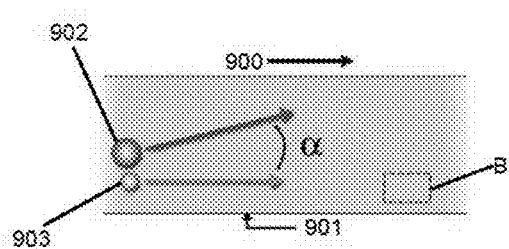
FIG. 9A is a schematic partial plan view of a microfluidic channel according to an exemplary embodiment of a microfluidic particle separator.
Figure 9B:
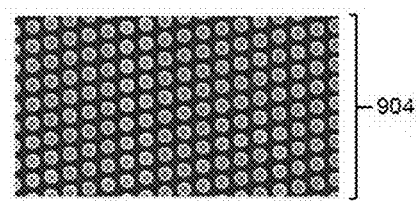
FIG. 9B is a magnified view of area B in FIG. 9A.

Referring now to FIGS. 9A to 9D, microfluidic particle separation may be achieved according to one embodiment of the present invention by arranging micropillars 904 of a desired size and/or shape in a pattern that may direct the separate flow of differently sized particles (902, 903). Thus, unlike the embodiment illustrated in FIGS. 7A and 7B, the micropillars may not be arranged to include spaces for the purpose of capturing microspots. Instead, for example, a microfluidic channel 901 may be provided with a plurality of evenly spaced micropillars 904, as illustrated in FIG. 9B. It is also preferred that the height of the micropillars are substantially equal to the height of the microfluidic channel, such that the particles within the fluid flow is forced between the micropillars. FIG. 9B provides a top plan view of a magnification of the micropillars 904 within the area B in FIG. 9A. (The sizes of the micropillars 904 and particles 902, 903 in this and other illustrations herein are greatly exaggerated for illustration purposes.)

Figure 9C:
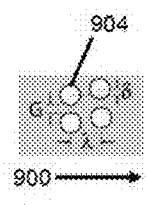
FIG. 9C is a schematic partial plan view of the micropillars in FIG. 9B.
Figure 9D:
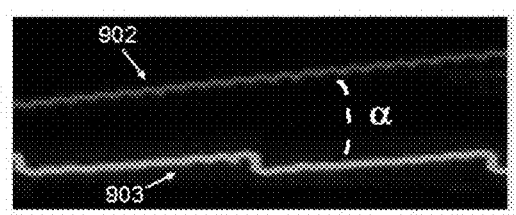
FIG. 9D is a schematic partial plan view of a particle separation occurring in the microfluidic channel in FIG. 9A.

As illustrated in the schematic of FIG. 9C, the micropillars in one embodiment may have a cylindrical shape, and the space between adjacent micropillars within the same column perpendicular to the direction of fluid flow 900 may be equal to a distance G. The distance between the center points of adjacent micropillars within the same row in the direction of fluid flow may be equal to a distance λ. The micropillars 904 in each column may also be shifted in the direction perpendicular to flow relative to the micropillars 904 in an adjacent column. For example, the distance in the direction perpendicular to flow between the center points of adjacent micropillars in a first and second column may be equal to a distance δ. The shape of the micropillars 904, as well as the dimensions G, λ, and δ may be varied in order to provide an array of micropillars for controlling the separation of the particles flowing in the microfluidic channel. Larger sized particles 902 may, for example, have a diameter that is at least twice as great as the smaller sized particles 903. Both particles may be carried by a fluid in the microfluidic channel 901 in the direction of flow 900. However, due to the size, shape, and arrangement of the micropillars 904, as well as the length of the microfluidic channel 901, the large sized particles 902 may separate from the smaller sized particles 903 by an angle α. This may be caused by the larger sized particles 902 tracking along the array of micropillars 904 in a bumping fashion, but the smaller sized particles 903 may flow more smoothly in between the micropillars 904, as illustrated in FIG. 9D.

Figure 10:
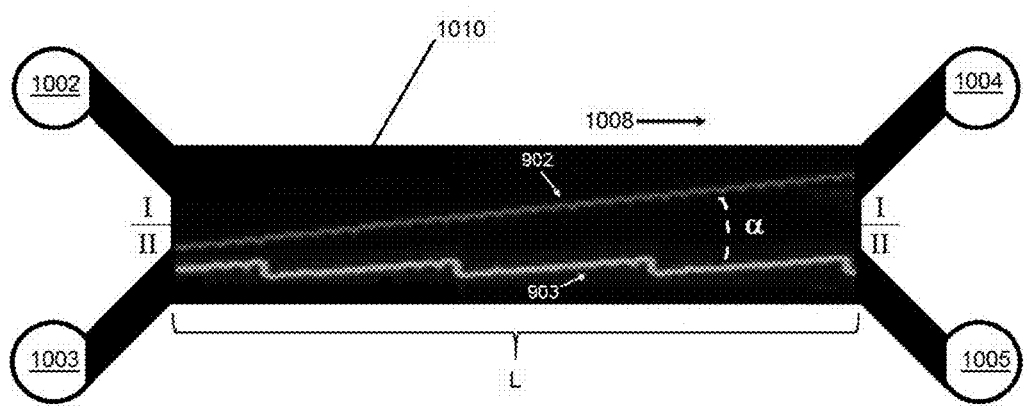
FIG. 10 is a schematic plan view of a microfluidic particle separator containing the microfluidic channel of FIG. 9A.

In one application, the microfluidic particle separator may be used to extract target particles from a sample, as illustrated in the top plan view of the device in FIG. 10. A fluid sample containing target microbeads 902 and undesired smaller particles 903 may be introduced into the device at port 1003. A running buffer may be introduced into port 1002 to the top half I of the a microfluidic channel 1010. The laminar flow of the running buffer and the fluid sample will provide two substantially separate and parallel fluid flows in the direction 1008 through the top half I and bottom half II, respectively, of the microfluidic channel 1010. The microfluidic channel 1010 may include an array of micropillars (not shown) that are configured to cause the bumped flow of the target microbeads 902. The configuration of the micropillars and the length L of the microfluidic channel 1010 should be selected, such that resulting separation angle α of the particles allows the target microbeads 902 to migrate from the flow of sample fluid in the bottom half II of the microfluidic channel 1010 to the top half I into the flow of running buffer. This allows the target microbeads 902 to be extracted and collected from the device from outlet port 1004, and the undesired smaller particles 903 to be discarded through waste port 1005. As would be understood by one of skill in the art, the target particles may alternatively be the smaller-sized particles; therefore, in some embodiments, the particles exiting outlet port 1004 may be discarded and the smaller particles exiting port 1005 may be collected for further processing.

As previously noted, the size and shape of the micropillars and configuration of the micropillar array may be modified to provide the appropriate separation angle α depending on the size of the target particles and undesired particles. The target particles, in some embodiments, may include microspots or microbeads having a diameter greater or less than the undesired particles. For example, the undesired particles in the sample fluid may include one or more of bacteria (less than ~2 microns), white blood cells, platelets, red blood cells (~3 to ~7 microns), neutrophils (~10 microns), parasites (~12 microns), or circulating tumor cells (~15 microns). Thus, the shape, spacing, and dimensions of the micropillars and/or micropillar array may be tuned to optimize the ability of the device to separate target particles from undesired particles based on the type of biological fluid sample.

In some embodiments, the sample fluid may be in the form of an emulsion and separation of the emulsion may be desired along with simultaneous particle separation. Therefore, in certain embodiments, the micropillars may be made of a hydrophobic material or coated with a hydrophobic material that is able to attract and retain an oil phase in the sample fluid. Hydrophobic materials that may be used to fabricate or coat the micropillar arrays may include hydrophobic polymers or oligomers known to those of skill in the art. As would be understood by one of skill in the art, the design and configuration of the micropillar array should account for the retention of oil in order to simultaneously filter the oil phase and separate out target particles from the sample fluid.

Figure 11:
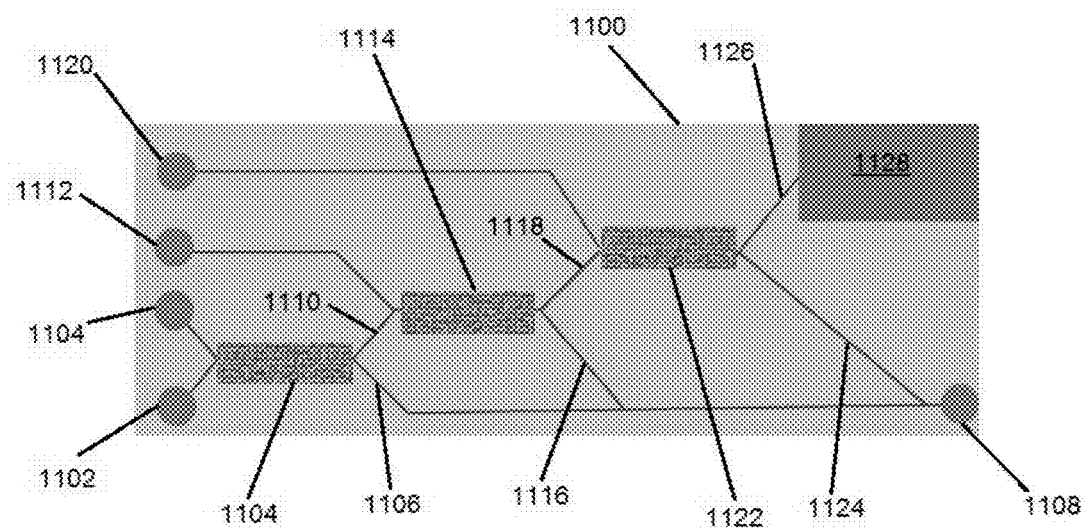
FIG. 11 is a schematic partial plan view of yet another exemplary embodiment of a cartridge comprising a plurality of microfluidic particle separators in fluid connection with a flowcell.

In yet another embodiment of the present invention, a plurality of microfluidic particle separators may be placed in series on a single device, such as a cartridge, in order to deliver target particles to a flowcell. For example, referring to FIG. 11, a top plan view of a cartridge 1100 is provided comprising a flowcell 1128, a plurality of particle separators 1104, 1114, 1122, and a plurality of ports 1102, 1104, 1112, 1120, 1108 that are all in fluid connection. The first particle separator 1104 may be configured similar to the separator illustrated in FIG. 10. A sample fluid containing target particles may be introduced through inlet port 1102 and delivered to a first separator 1104 comprising a microchannel having an array of micropillars (not shown). The target particles may, for example, be microspots or microbeads having an attached primer, as described above. The configuration of the micropillars may allow the separation of the target particles from the sample fluid and into a buffer fluid introduced into the first separator 1104 through buffer port 1104. When the sample fluid introduced into the inlet port 1102 is in the form of an emulsion and it is desired to filter the oil phase from the sample fluid, the array of micropillars in the first separator 1104 may be made or coated with a hydrophobic material. The undesired particles in the sample fluid and waste fluid (including any oil phase) may exit the first separator 1104 through an outlet channel 1106 in fluid connection with a waste port 1108.

The buffer containing the target particles may then be delivered to a second separator 1114 comprising a solid substrate for capturing the target particles. The target particles may be joined to the solid substrate by biotin-streptavidin bonds, covalent bonds, electrostatic interactions, Van der Waals forces, and so on. The target particles may be captured by the second separator 1114, while the carrying buffer is expelled through outlet channel 1116 to waste port 1108. Once the target particles have been captured, a releasing buffer, such as NaOH, may be introduced through release buffer port 1112 and delivered to the second separator 1114 to extract the collected target particles.

The releasing buffer carries the target particles through an inlet channel 1118 to a third separator 1112. The third separator 1122 may be configured similarly to the first separator 1104 in that it may include an array of micropillars to cause a bumping flow of the target particles and cause diffusion of the target particles from the releasing buffer to a flowcell loading buffer that is simultaneously introduced into the third separator 1122 through a flowcell loading buffer port 1120. The releasing buffer may then be expelled through outlet channel 1124 to a waste port 1108, and the flowcell loading buffer carrying the target particles may be transferred through channel 1126 to a flowcell 1128. The flowcell 1128 may be configured according to the previously described embodiments of the present invention in order to capture the target particles.

As would be understood by one of skill in the art, the separators may optionally be provided with microvalves at their inlets and/or outlets to control the introduction of the appropriate type of buffer fluid and to prevent a buffer fluid from entering the incorrect inlet or outlet channel. In other embodiments, the separators and flowcells may be provided on separate cartridges; however, it is preferred for convenience to provide the separators and flowcells on a single cartridge. As would also be appreciated by one of skill in the art, a single cartridge may be provided with more or less than three separators.

The present disclosure describes a number of new, useful and nonobvious features and/or combinations of features that may be used alone or together. While certain features and advantages are described herein, it will be appreciated that the described features and advantages may not be present in every embodiment. The embodiments described herein are all exemplary, and are not intended to limit the scope of the inventions. It will be appreciated that the inventions described herein can be modified and adapted in various and equivalent ways, and all such modifications and adaptations are intended to be included in the scope of this disclosure and the appended claims.

We claim:

1. A microfluidic particle separator comprising:
 a microfluidic channel extending along a longitudinal axis;
 a release buffer inlet located on a first side of the longitudinal axis and configured to receive a release buffer containing a plurality of microspots,
 a loading buffer inlet located on a second side of the longitudinal axis and configured to receive a loading buffer,
 wherein the microfluidic channel is configured to simultaneously receive the release buffer containing the plurality of microspots and the loading buffer, and the microfluidic channel comprises an array of micropillars configured to selectively transfer the plurality of microspots from the release buffer to the loading buffer based upon the sizes of the microspots, and
 a loading buffer outlet configured to receive the loading buffer containing the plurality of microspots and a minimal amount of or substantially none of the release buffer.

2. The microfluidic particle separator of claim 1, wherein the array of micropillars comprises a hydrophobic material.

3. A cartridge for a sequencing instrument comprising a flowcell and a microfluidic particle separator according to claim 1, wherein the loading buffer outlet of the microfluidic particle separator is in fluid connection with a fluid inlet of the flowcell.

* * * * *

UNITED STATES PATENT AND TRADEMARK OFFICE
CERTIFICATE OF CORRECTION

PATENT NO. : 9,962,701 B2  
APPLICATION NO. : 15/386515  
DATED : May 8, 2018  
INVENTOR(S) : Michel Georges Perbost et al.

It is certified that error appears in the above-identified patent and that said Letters Patent is hereby corrected as shown below:

Assignee: "QIAGEN SCIENCES, LLC , Waltham, MA (US)" should read -- QIAGEN SCIENCES, LLC, Germantown, MD (US) --

Signed and Sealed this  
Thirty-first Day of July, 2018

Andrei Iancu  
*Director of the United States Patent and Trademark Office*